(12) United States Patent
Kozic et al.

(10) Patent No.: US 11,707,362 B2
(45) Date of Patent: Jul. 25, 2023

(54) SURGICAL TARGETING DEVICE

(71) Applicant: Stryker European Operations Limited, Carrigtwohill (IE)

(72) Inventors: Nina Kozic, Bern (CH); Yves Flourie, Neuchâtel (CH); Denis Digeser, Freiburg (DE); Markus Ochs, Amsterdam (NL)

(73) Assignee: Stryker European Operations Limited

( * ) Notice: Subject to any disclaimer, the term of this patent is extended or adjusted under 35 U.S.C. 154(b) by 232 days.

(21) Appl. No.: 17/022,887

(22) Filed: Sep. 16, 2020

(65) Prior Publication Data

US 2021/0077277 A1 Mar. 18, 2021

(30) Foreign Application Priority Data

Sep. 17, 2019 (EP) .................................... 19197676

(51) Int. Cl.
*A61F 2/46* (2006.01)
*A61F 2/30* (2006.01)

(52) U.S. Cl.
CPC .......... *A61F 2/4607* (2013.01); *A61F 2/4609* (2013.01); *A61F 2002/30462* (2013.01); *A61F 2002/30672* (2013.01); *A61F 2002/4687* (2013.01)

(58) Field of Classification Search
CPC ................. A61F 2/4607; A61F 2/4609; A61F 2002/30672; A61F 2002/4687; A61F 2/4684; A61F 2002/30649; A61F 2002/4276; A61F 2/4261; A61B 17/8897; A61B 17/90; A61B 17/1697; A61B 17/848; A61B 17/1782; A61B 17/1686
See application file for complete search history.

(56) References Cited

U.S. PATENT DOCUMENTS

| | | | |
|---|---|---|---|
| 8,454,619 B1* | 6/2013 | Head | A61F 2/4684 606/91 |
| 2012/0109137 A1* | 5/2012 | Iannotti | A61B 17/1728 606/87 |
| 2013/0245631 A1 | 9/2013 | Bettenga | |

(Continued)

FOREIGN PATENT DOCUMENTS

| CN | 105559951 B | 4/2017 |
|---|---|---|
| CN | 109820591 A | 5/2019 |
| EP | 3117801 A1 | 1/2017 |

(Continued)

OTHER PUBLICATIONS

Extended European Search Report including Written Opinion for Application No. EP19197676.0, dated Jun. 25, 2020, pp. 1-10.

(Continued)

*Primary Examiner* — Javier G Blanco
(74) *Attorney, Agent, or Firm* — Lerner David LLP

(57) ABSTRACT

Disclosed is a surgical targeting device for assisting placement of an elongated guidance member in a bone. The targeting device comprises a bottom portion having a dome-shaped convex outer surface and comprising a guidance through-hole extending along a guidance through-hole central axis for receiving the guidance member. A top portion of the targeting device is configured to be gripped by a tool. Further, a surgical system is disclosed which comprises the surgical targeting device.

19 Claims, 10 Drawing Sheets

(56) References Cited

U.S. PATENT DOCUMENTS

2015/0265292 A1* 9/2015 Olson ............... A61B 17/1684
606/80
2018/0303533 A1 10/2018 Hopkins

FOREIGN PATENT DOCUMENTS

EP      3210550 A1   8/2017
WO   2018035175 A1   2/2018

OTHER PUBLICATIONS

Small Bone Innovations, An Anatomical Carpometacarpal Joint Replacement With Dual Mobility System, Moovis Dual-Mobility, Surgical Technique, 2013, 20 pages.

* cited by examiner

SURGICAL TARGETING DEVICE

CROSS-REFERENCE TO RELATED APPLICATIONS

The present application claims priority to European Patent Application No. 19197676.0 filed on Sep. 17, 2019, the disclosure of which is hereby incorporated herein by reference.

TECHNICAL FIELD

The present disclosure provides a surgical targeting device for assisting placement of an elongated guidance member in a bone. The present disclosure further provides a surgical system comprising the surgical targeting device and at a least a socket part of a ball and socket joint implant. Also disclosed is a surgical method of using the surgical targeting device.

BACKGROUND

A K-wire (also referred to as Kirschner wire) is an elongated guidance member that is typically a pointed stainless-steel wire used in orthopedic surgery for temporary fixation to a bone. K-wires are used for many surgical purposes.

For example in carpometacarpal joint replacement surgery, a K-wire is temporarily fixed in a trapezium bone at a desired location and orientation to serve as guidance for a reamer sliding onto the K-wire. The reamer can then be moved from the free end of the K-wire protruding from the respective bone towards the bone to ream the bone at the desired location and orientation of the K-wire.

Once a desired reaming depth is reached, the reamer is pulled back and removed from the K-wire. Afterwards, the K-wire is removed from the bone to allow placement of a joint prosthesis cup (i.e., a socket part of a ball and socket joint implant) in the bone recess created by the reamer.

Currently, in carpometacarpal joint replacement surgery, the K-wire is placed and fixed in a trapezium bone by the surgeon based on his or her surgical experience and skills. The proper location and orientation of the K-wire may be verified by X-ray images, after which the K-wire is repositioned, if necessary. Any required repositioning of the K-wire extends the duration of the surgical procedure and weakens the bone in which it will repeatedly be placed.

SUMMARY

Accordingly, it has been discovered that there is a need for a surgical targeting device that facilitates placement and fixation of an elongated guidance member such as a K-wire to a bone, such as—but not limited to—a trapezium bone, at a desired location and orientation.

The present disclosure provides a surgical targeting device for assisting placement of an elongated guidance member in a bone. The device comprises a bottom portion having a dome-shaped convex outer surface and comprising a guidance through-hole extending along a guidance through-hole central axis for receiving the guidance member. The device further comprises a top portion configured to be gripped by a tool.

The guidance through-hole may extend along the guidance through-hole central axis through the bottom portion and the top portion. Optionally, the guidance through-hole has a circular cross-section along its entire extension through the surgical targeting device. The guidance through-hole may have a uniform cross-section along its extension through the surgical targeting device, which in case of the cross-section being circular has a constant diameter along the guidance through-hole's extension through the surgical targeting device.

The top portion may comprise a shaft extending from the bottom portion. Optionally, the shaft is formed as, or comprises, a neck or a collar. A neck may have a greater length than width, and a collar may have a greater width than length, wherein the length is measured from the bottom portion along a straight line passing through a center of the bottom portion.

The shaft may be configured to temporarily be inserted into a stem of an implant or of a dummy thereof. Optionally, the shaft of the targeting device top portion has the shape and, further optionally, the outer dimensions of a shaft of a ball part of a ball and socket joint implant. In some variants, the shaft has a conical upper portion at its free end facing away from the bottom portion, which narrows in a direction away from the bottom portion.

The shaft may be monolithic with or removably connected to the bottom portion. Optionally, the shaft has a conical lower portion which is connected to the bottom portion only by its narrow end. The shaft and the bottom portion may be connected by a threaded connection, a detachable or permanent snap fit, or a bayonet joint.

The bottom portion may comprise at least one auxiliary through-hole extending through the bottom portion along an auxiliary through-hole central axis and spaced from the guidance through-hole. The at least one auxiliary through-hole optionally is configured to receive an attachment member so that the device becomes temporarily engaged with the bone. The attachment member may be an elongated member, such as a K-wire or bone screw.

The auxiliary through-hole central axis may extend obliquely to the guidance through-hole central axis. Optionally, the auxiliary through-hole central axis extends obliquely to the guidance through-hole central axis in a plane parallel to a plane in which the guidance through-hole central axis extends. The angle at which the auxiliary through-hole central axis extends to the guidance through-hole central axis may be in the range from 70° to 20°. Optionally, the angle is 45°.

The guidance through-hole central axis and the auxiliary through-hole central axis may not intersect. In particular, the at least one auxiliary through-hole and the guidance through-hole do not intersect, i.e., are distanced from each other.

The at least one auxiliary through-hole optionally extends from a top opening to a bottom opening in the device. Optionally, only the bottom portion comprises the at least one auxiliary through-hole. The top opening may be further spaced from the guidance through-hole central axis than the bottom opening is spaced from the guidance through-hole central axis. The distance to the guidance through-hole central axis may be measured in a straight line from the guidance through-hole central axis and orthogonally to the guidance through-hole central axis to the center of the respective top or bottom opening.

The bottom portion may comprise one or more wings laterally protruding from the bottom portion and each optionally comprising at least one of the at least one auxiliary through-hole. Optionally, the bottom portion comprises one wing with two, three, four or more auxiliary through-holes.

The bottom portion may comprises at least one protrusion, such as a fin or a spike, for temporary engagement with the bone. Optionally, the outer surface of the bottom portion comprises at least one portion with increased roughness compared to other portions of outer surface of the bottom portion or compared to the outer surface of the top portion or the inner surface of the guidance through-hole.

The bottom portion may comprise a visual depth marker indicative of a plane extending orthogonally to the guidance through-hole central axis. Optionally, the visual depth marker delimits the bottom portion from the top portion of the device.

The visual depth marker may be realized as a circumferential marking, groove or rim. Optionally, the visual depth marker is a combination of at least two of the marking, groove or rim. The at least two of the marking, groove or rim may be arranged circumferentially in parallel along the outer dimensions of the bottom portion and/or in succession along a single circumferential line.

The top portion may comprise a tool gripping structure configured to be gripped by the tool for removing the surgical targeting device from the bone. Optionally, the tool gripping structure is located at an end of the top portion facing the bottom portion. The tool gripping structure may in some variants comprise a tool abutment region that runs obliquely (e.g., perpendicularly) to a direction along which the surgical targeting device is to be removed from the bone after it has fulfilled its targeting function. In such or other variants, the tool gripping portion may comprise a substantially cylindrical region that extends along this direction of removal. The tool may take the form of pliers, forceps, threaded tools, bayonet-type tools, and so on.

The tool gripping structure may comprise a neck or a collar. The neck may have a greater length than width, and the collar may have a greater width than length, wherein the length is measured from the bottom portion along a straight line passing through a center of the bottom portion.

The tool gripping structure may comprise a thread or a bayonet-type interface. Optionally, the tool gripping structure comprises at least one of an undercut, groove, rim, indentation, thread, bayonet-type interface, or through-hole extending obliquely to the guidance through-hole central axis in the top portion.

The guidance through-hole central axis may extend in a symmetry plane of the surgical targeting device. Optionally, the guidance through-hole central axis extends in the symmetry plane of the bottom portion of the surgical targeting device, further optionally only of the bottom portion.

The present disclosure also provides a surgical system. The system comprises one of the surgical targeting device presented herein and a socket part of a ball and socket joint implant. In such a system, the bottom portion of the surgical targeting device fits into a volume defined by the outer dimensions of the socket part of the ball and socket joint implant.

Optionally, the volume of the bottom portion of the surgical targeting device fits into an open volume defined by inner dimensions of the socket part. The term "fit" may mean "is equal to or less than" the respective dimensions.

The present disclosure further provides a surgical system comprising the above surgical system or the surgical targeting device presented herein and a ball part of a ball and socket joint implant with a spherical head (i.e. a head portion of the ball part). In such a system, an outer radius of the bottom portion of the surgical targeting device may equal to or less than an outer radius of the head of the ball part. As such, the volume of the bottom portion may fit in the volume of the head of the ball part. Optionally, the bottom portion and the head are spherical.

The dome-shaped convex outer surface of the bottom portion of the surgical targeting device may be spherically shaped. In addition, or as an alternative, the socket part of the ball and socket joint implant may have a conically shaped outer surface.

Any surgical system presented herein optionally further comprises a ball part of the ball and socket joint implant. The ball part comprises a head, a shaft extending from the head, and a stem which is capable of receiving at least a portion of the shaft. Optionally, the top portion of the surgical targeting device and the portion of the shaft of the ball part capable of being received by the stem have corresponding outer dimensions capable of being received in the stem.

The present disclosure further provides a surgical method comprising the steps of:

preparing a bone for temporarily mounting a surgical targeting device therein, the surgical targeting device having a guidance through-hole;

temporarily placing the surgical targeting device in the bone (optionally including adjusting at least one of the position and orientation of the surgical targeting device relative to the bone);

inserting a guidance member through the guidance through-hole;

temporary fixing the guidance member to the bone;

removing the surgical targeting device from the bone while the guidance member remains fixed in its position and orientation relative to the bone.

The surgical targeting device utilized in this method may be configured as disclosed herein, or may have a different configuration. As such, the surgical targeting device may in particular comprise a bottom portion having a dome-shaped convex outer surface and comprising the guidance through-hole that extends along a guidance through-hole central axis for receiving the guidance member. In some variants, the surgical targeting device may further comprise a top portion configured to be gripped by a tool.

BRIEF DESCRIPTION OF THE DRAWINGS

The foregoing summary, as well as the following detailed description of the embodiments and examples, will be better understood when read in conjunction with the drawings. For the purposes of illustrating the present disclosure, exemplary embodiments are shown in the drawings. It should be understood, however, that the invention is not limited to the specific embodiments disclosed, and reference is made to the claims for that purpose. In the drawings:

DETAILED DESCRIPTION

Figure 1:
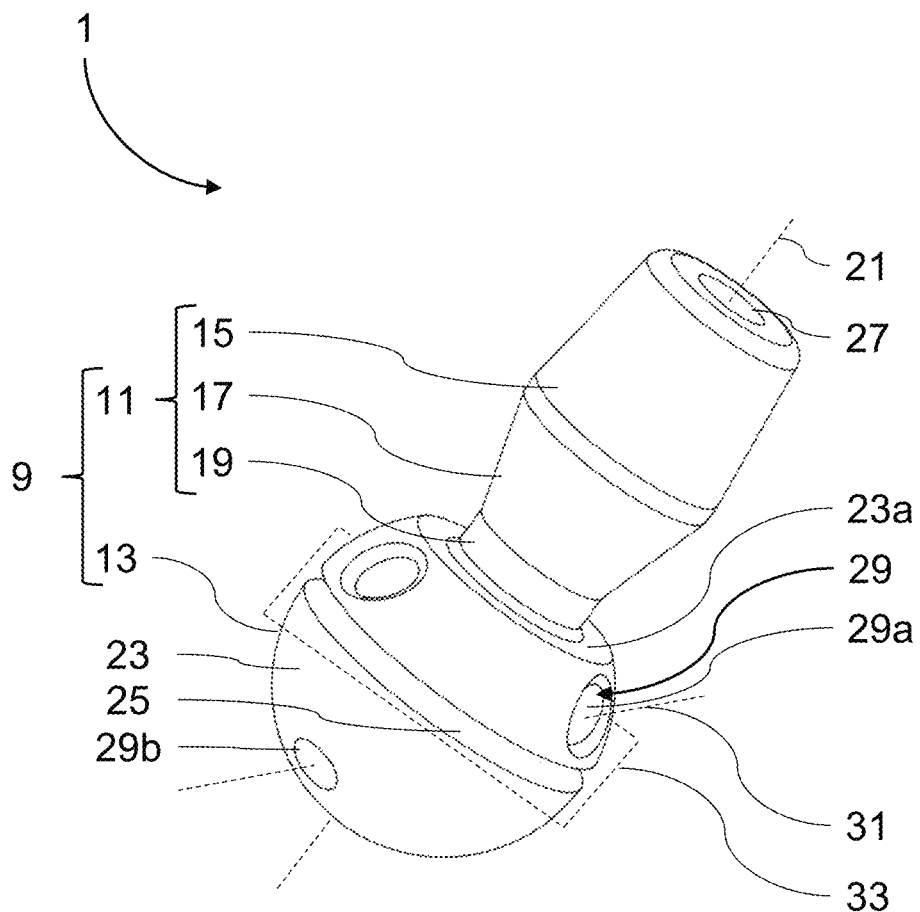
FIG. 1 is a perspective view of a first surgical targeting device embodiment with a longitudinal through-hole for a guidance member and lateral auxiliary through-holes for auxiliary attachment members surrounding the longitudinal through-hole.

In the following description of exemplary embodiments, the same reference numerals are used to denote the same or similar features.

FIG. 1 shows a perspective view of a first embodiment of a surgical targeting device 1 to be temporarily placed in the trapezium bone for assisting placement of a K-wire or other flexible or rigid guidance member in joint replacement surgery. It will be appreciated that the targeting device 1 illustrated in FIG. 1 and in the remaining drawings could also be used for other indications, such as hip joint replacement surgery, provided that the device dimensions are properly modified.

The surgical targeting device 1 illustrated in FIG. 1 has a monolithic body 9 with a top portion 11 and a bottom portion 13. The top portion 11 comprises three sections and defines a tool gripping structure configured to be gripped by a tool for removing the surgical targeting device 1 from bone. These three sections comprise a top truncated cone 15, a bottom truncated cone 17, wherein the top and bottom truncated cones 15, 17 are joined to each other by their respective larger surface ends, and a bottom cylinder 19 joined on one end to the smaller surface end of the bottom truncated cone 17. While here top and bottom truncated cones 15, 17 are provided, one or both of the top and bottom truncated cones 15, 17 may be omitted. For example, the top portion may only comprise the bottom cylinder 19, when then have a larger longitudinal extension so that it can securely be gripped by a tool.

The bottom portion 13 comprises a guidance through-hole 27 extending along a guidance through-hole central axis 21. As illustrated in FIG. 1, the top portion 11 extends symmetrically about the guidance through-hole central axis 21.

The bottom portion 13 has a uniformly shaped outer surface 23 and extends from one end of the top portion bottom cylinder 19. In more detail, the bottom portion 13 has an incomplete spherical shape of a spherical frustum with an end surface 23a that runs orthogonally to the guidance through-hole central axis 21. The bottom portion 13 may also have the shape of a spherical cap or a spheroid, e.g., an oblate (flattened) spheroid or a prolate (elongated) spheroid. In all embodiments presented herein in the context of the trapezium bone, the bottom portion 13 may have a maximum diameter between 5 and 10 mm A curvature of the bottom portion 13 may lie between Radius 2.5 mm and 12 mm.

The bottom portion 13 includes a circumferential groove 25 in a plane extending orthogonally to the guidance through-hole central axis 21. Such circumferential groove 25 serves as a visual depth marker 25, 49 to help the surgeon determine the depth in which the bottom portion 13 of the surgical targeting device 1 shall be positioned in the trapezium bone. A distance between a plane comprising the circumferential groove 25 (or any other depth marker) and a plane comprising the end of the bottom portion 13 facing towards the trapezium bone may lie between 2 mm and 7 mm in all embodiments presented herein.

In the surgical targeting device 1, the guidance through-hole 27 extends through the entire body 9 concentrically to the longitudinal guidance through-hole central axis 21. In FIG. 1 only its top opening in the top portion 11 is visible while its bottom opening in the bottom portion 13 is not (due to the chosen perspective view).

The surgical targeting device 1 also comprises three auxiliary through-holes 29, only two of which are visible in the perspective view of FIG. 1. The auxiliary through-holes 29 constitute surface irregularities in the otherwise uniform outer surface 23 of the bottom portion 13. Each auxiliary through-hole 29 extends through the bottom portion 13, but not through the top portion 11.

Each of the auxiliary through-holes 29 extends concentrically to an auxiliary through-hole central axis 31, i.e., a central axis 31 of the auxiliary through-hole 29. This auxiliary through-hole central axis 31 is offset and extends obliquely to the guidance through-hole 27 and its guidance through-hole central axis 21. In this particular case, the three auxiliary through-holes 29 are arranged at equal distances to each other on a circumference of the guidance through-hole 27 and its guidance through-hole central axis 21 such that the three auxiliary through-holes 29 remain independent from the guidance through-hole 27 along their entire length. As such, the three auxiliary through-holes 29 do not intersect the guidance through-hole 27.

In FIG. 1, each auxiliary through-hole central axis 31 extends equidistantly from the guidance through-hole central axis 21 from a plane 33 which is orthogonal to the guidance through-hole central axis 21 and intersects the auxiliary through-hole central axis 31 at a point closest to the guidance through-hole central axis 21. The plane 33 lies in the center of the respective auxiliary through-hole 29, such that both ends of the auxiliary through-hole 29 are equidistant from the guidance through-hole central axis 21. This placement allows handling of temporary attachment members 37 (e.g., K-wires) for the auxiliary through-holes 29 at a greater distance from the guidance through-hole central axis 21 and thus from the guidance member 39 (K-wire), as will be described with reference to FIG. 2 in more detail. In order to benefit from this effect, the plane 33 may lie closer to the bottom end/bottom opening 29b of the respective auxiliary through-hole 29 at the bottom portion 13 than to the top end/top opening 29a of the auxiliary through-hole 29, or vice versa. In other words, the top opening 29a may be further spaced from the guidance through-hole central axis 21 than the bottom opening 29b is spaced from the guidance through-hole central axis 21. The distance to the guidance through-hole central axis 21 is measured in a straight line from the guidance through-hole central axis 21 and orthogonally to the guidance through-hole central axis 21 to the center of the respective top or bottom opening 29a, 29b. Of course, each auxiliary through-hole central axis 31 may extend in parallel to the guidance through-hole central axis 21. Alternatively, a combination of the above is also possible. Further, instead of three auxiliary through-holes 29, at least one, in particular one or two or four auxiliary through-holes 29 may be provided in the bottom portion 13.

In the present embodiment, the minimal cross-section diameter of an auxiliary through-hole 29 is less (or more) than the minimal cross-section diameter of the guidance through-hole 27. This diameter difference has the purpose to prevent inadvertent insertion of the guidance member 39 intended for the guidance through-hole 27 in one of the auxiliary through-holes 29, provided that also the respectively provided guidance members have different diameters. The through-holes 27, 29 may be cylindrically shaped.

Figure 2:
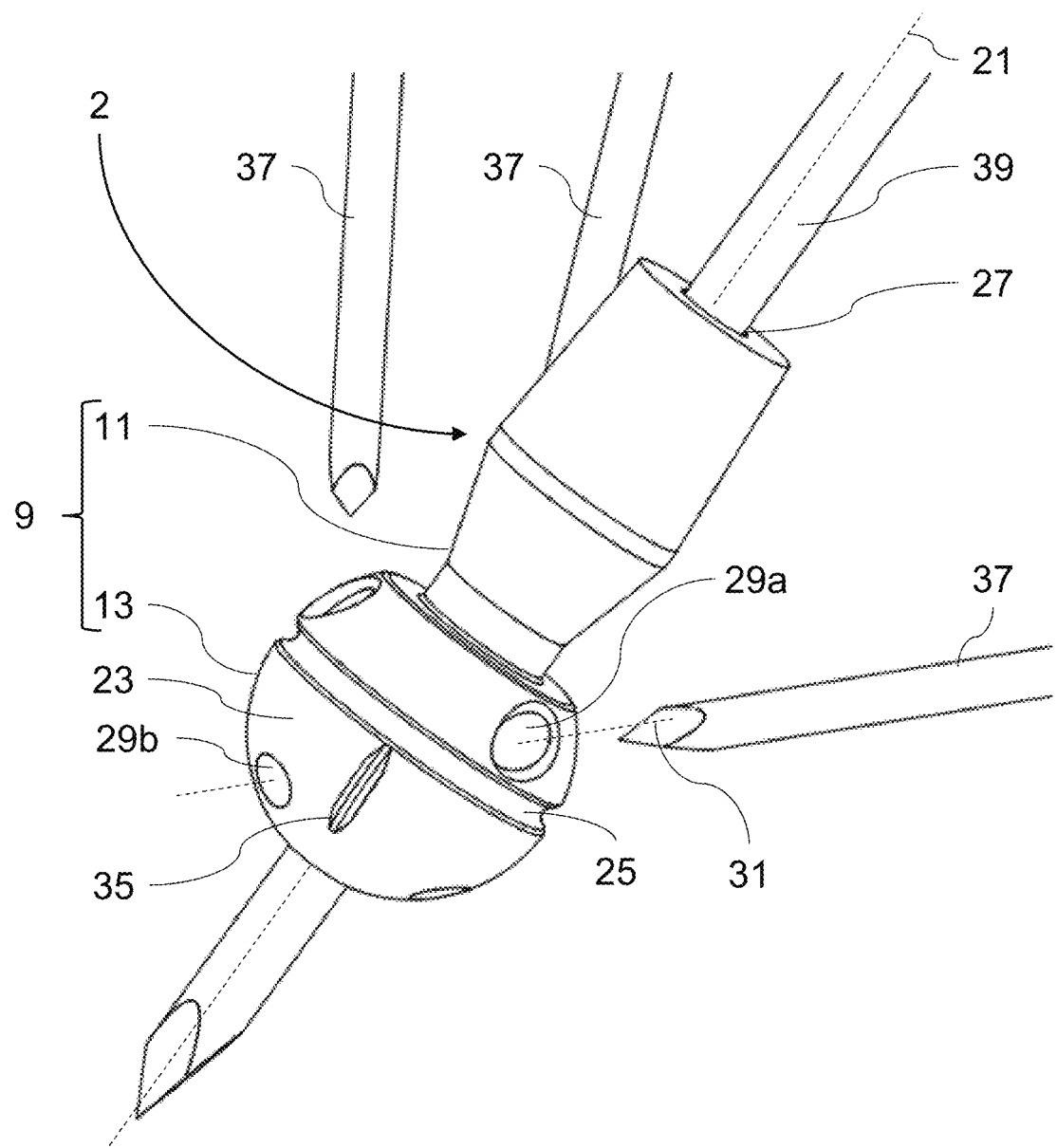
FIG. 2 is a perspective view of a second surgical targeting device embodiment corresponding to the first surgical targeting device embodiment of FIG. 1 with a lateral fin in a state in which the auxiliary attachment members are pulled out of the lateral auxiliary through-holes and the guidance member is inserted through and extends from the longitudinal through-hole.

FIG. 2 shows a perspective view of a further surgical targeting device 2 corresponding to the surgical targeting device in FIG. 1 with the addition of an optional lateral fin 35 on the bottom portion 13. This lateral fin 35 protrudes as a surface irregularity from the otherwise uniform outer surface 23 of the bottom portion 13 to form with its longitudinal extension direction and with the guidance through-hole central axis 21 a common plane. In the present embodiment, the fin 35 exemplarily starts at the groove 25 and extends on the outer surface 23 of the bottom portion 13 towards the bottom end of the guidance through-hole 27. Here, the bottom openings 29b of the auxiliary through-holes 29 lie closer to the bottom end of the guidance through-hole 27 than the end of the fin 35 closest to the bottom end of the guidance through-hole 27. There may be not just one, but at least one, in particular two, three or more fins provided on the outer surface 23 of the bottom portion 13, preferably at equal circumferential distances to each other. The purpose of this fin 35 is to improve the temporary fixation of the surgical targeting device 2 to the trapezium bone.

As such, the one or more fins 35, in a similar manner as the one or more attachment members 37, prevent the device 2, when inserted into the trapezium bone, from changing its location or orientation relative to the trapezium bone (so that in some variants the auxiliary through-holes 29 can be omitted), as well now be described in greater detail.

During surgery, the surgical targeting device 2 is placed in the trapezium bone at a desired location and orientation. The desired position and orientation may be checked using medical imaging methods. Then, auxiliary attachment members 37, such as K-wires, with a diameter of, for example, 1.1 mm are inserted from a top to bottom direction of the surgical targeting device 2 through the respective auxiliary through-holes 29 and into the bone to temporarily fix the surgical targeting device 2 to the bone.

Once the surgical targeting device 2 is located and oriented as desired by the surgeon, a guidance member 39, such as a K-wire, with a diameter of, for example, 1.6 mm is inserted in a top to bottom direction of the surgical targeting device 2 through the guidance through-hole 27 into the bone. Then, the auxiliary K-wires 37 are removed from the bone and from the auxiliary through-holes 29, which is the state shown in FIG. 2 (illustration of the trapezium bone has been omitted). Finally, the surgical targeting device 2 is pulled from the bone in a removal direction generally defined by the guidance through-hole central axis 21, and from the free end of the guidance K-wire 39, by means of a suitable tool gripping, for example, the bottom cylinder 19 illustrated in FIG. 1. Hence, only the guidance K-wire 39 remains fixed and protruding from the bone.

Then, a reamer with a central through-hole will be guided on this guidance K-wire 39 towards the bone at the desired location and orientation set by the guidance K-wire 39. The reamer is used to create a cavity required for an actual bone implant (here: a ball part of a ball and socket joint implant). After successful reaming, the guidance K-wire is removed and the bone implant is introduced into the bone cavity created by the reamer.

For the above described purpose, the surgical targeting device presented herein may have alternative shapes, exemplary embodiments of which are shown in FIGS. 3 to 8 and discussed below.

Figure 3:
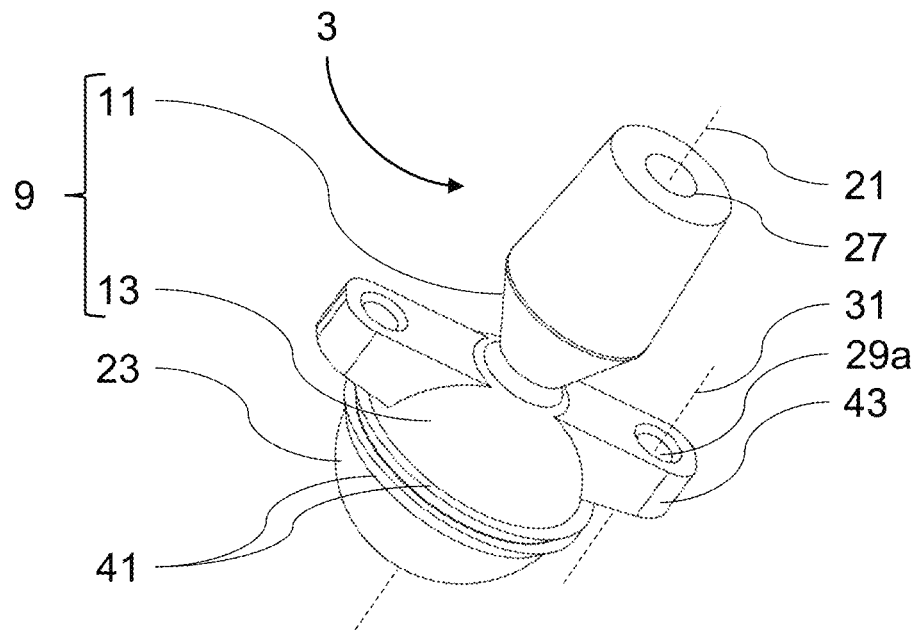
FIG. 3 is a perspective view of a third surgical targeting device embodiment with lateral wings each having a lateral auxiliary through-hole extending symmetrically to the longitudinal through-hole.

FIG. 3 shows a perspective view of a surgical targeting device 3 similar to the first and second surgical targeting devices 1, 2 shown in FIGS. 1 and 2, respectively. Therefore, some of the features already discussed with regard to the first and second surgical targeting devices 1, 2 will not be repeated.

The surgical targeting device 3 of FIG. 3 also comprises a monolithic body 9 with a top portion 11 and a bottom portion 13. Here, the top portion 11 comprises two sections: a top truncated cone 15 and a bottom truncated cone 17. The top and bottom truncated cones 15, 17 are joined to each other by their respective larger surface ends and form a neck at the transition between the top portion 11 and the bottom portion 13.

In the present embodiment, the bottom portion 13 comprises two parallel circumferential ring-shaped rims 41 as visual depth markers. Of course, alternatively one ring-shaped rim 41 may be provided.

A surface irregularity is formed on the upper half of the bottom portion 13 facing the top portion 11. That is, two lateral wings 43 extend symmetrically to the guidance through-hole central axis 21 with a uniform height in a lateral direction orthogonal to the guidance through-hole central axis 21. At the respective distant end of each the wings 43, an auxiliary through-hole 29 is provided with an auxiliary through-hole central axis 31 extending in parallel to the guidance through-hole central axis 21.

Figure 4:
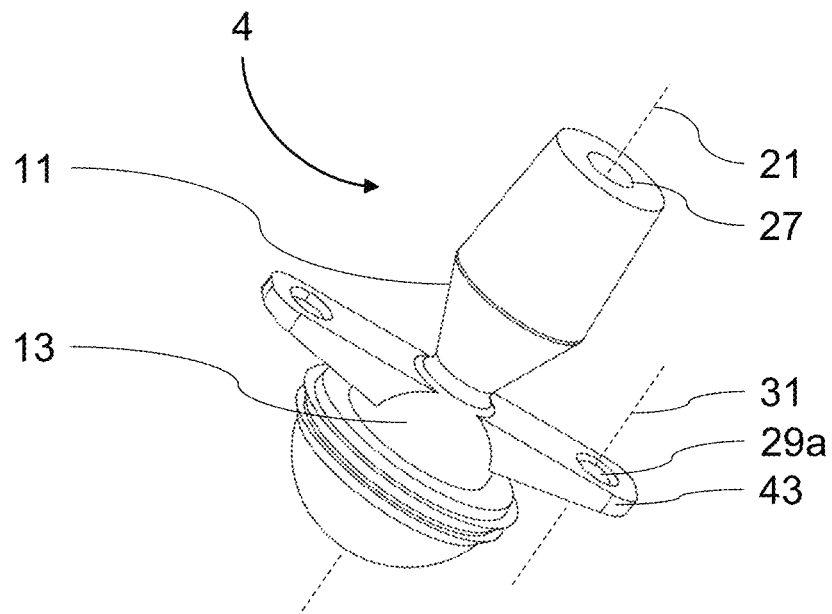
FIG. 4 is a perspective view of a fourth surgical targeting device embodiment similar to the third surgical targeting device embodiment of FIG. 3 with longitudinally tapered wings.

FIG. 4 shows a perspective view of another surgical targeting device 4 similar to the surgical targeting device 3 of FIG. 3. One difference resides in the fact that the bottom half of the bottom portion 13 comprises one hemisphere and the upper half of the bottom portion 13 comprises another hemisphere smaller than the hemisphere of the bottom half of the bottom portion 13. As another difference, the height of each of the wings 43 tapers in a direction away from the guidance through-hole central axis 21 from a bottom to top direction along the guidance center axis 21.

Figure 5:
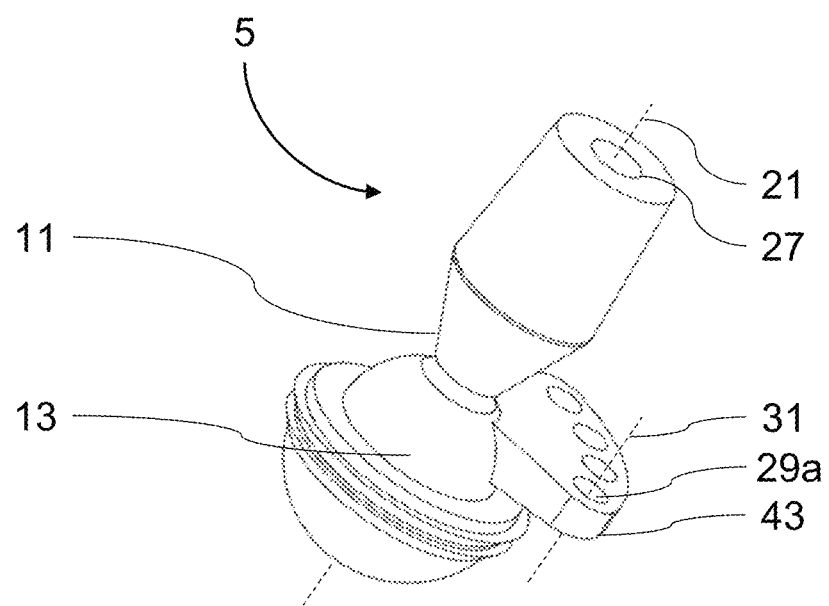
FIG. 5 is a perspective view of a fifth surgical targeting device embodiment with a single lateral wing having four auxiliary through-holes surrounding the longitudinal through-hole.

FIG. 5 shows a perspective view of a still further surgical targeting device 5 similar to the surgical targeting device 4 of FIG. 4. One difference resides in the fact that it comprises a single lateral wing 45 protruding laterally to the guidance center axis 21 from the bottom portion 13. Another difference is that instead of one, there are now four auxiliary through-holes 29 having auxiliary central axes 31 that extend in parallel to the guidance through-hole central axis 21. These auxiliary central axes 31 are arranged at equal circumferential intervals about and equidistantly to the guidance through-hole central axis 21.

Figure 6:
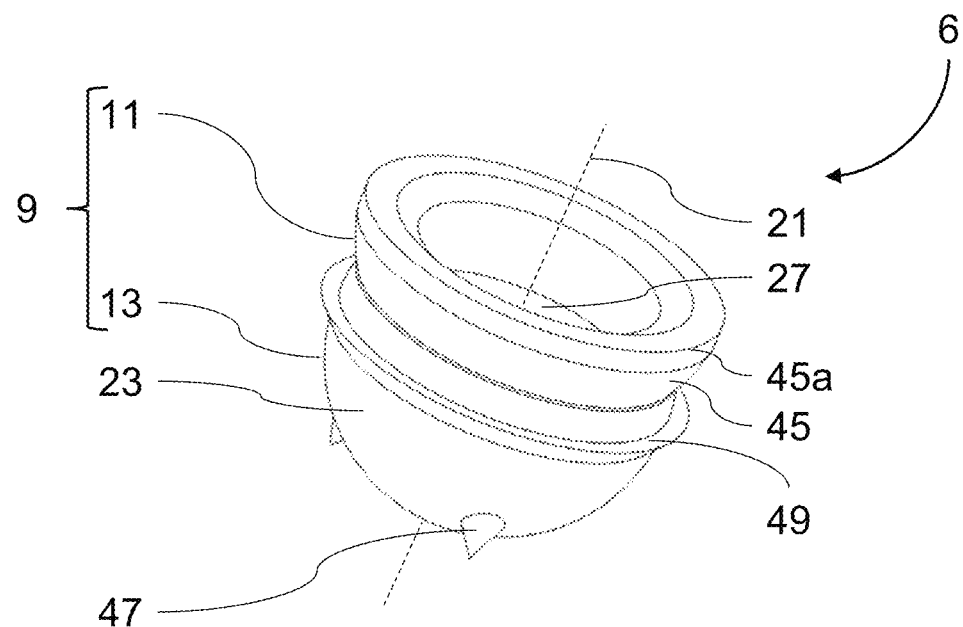
FIG. 6 is a perspective view of a sixth surgical targeting device embodiment with spikes and a truncated-cone-shaped collar.

FIG. 6 shows a perspective view of another surgical targeting device 6 having a monolithic body 9 with a top portion 11 and a bottom portion 13. Here, the top portion 11 comprises a truncated cone-shaped collar 45. This truncated cone-shaped collar 45 functions as a tool gripping structure provided for the engagement by a removal tool for removing the surgical targeting device 6 from the trapezium bone.

The bottom portion 13 comprises a hemisphere with an outer surface 23. Surface irregularities on the bottom portion 13 are provided in the form of (e.g., cone-shaped) spikes 47. While this embodiment comprises three spikes 47, only two are visible in FIG. 6. These spikes 47 protrude from the outer surface 23 towards a bottom direction along the guidance through-hole central axis 21. They are arranged at equal intervals circumferentially on the outer surface 23 equidistant to the guidance through-hole central axis 21. Alternatively, there may be at least one spike 47, in particular one or two or four or more spikes 47.

A circumferential rim 49 is located on the bottom portion 13 as a visual depth marker. A smaller surface end of the truncated cone-shaped collar 4 of the top portion 11 faces the bottom portion 13. Alternatively, the rim 49 may also be a groove 25, as explained above with regard to the first and second surgical targeting devices 1, 2.

In the surgical targeting device 6 of FIG. 6, a guidance through-hole 27 extends through the bottom portion 13 and through the entire body 9 concentrically to the longitudinal guidance through-hole central axis 21. In FIG. 6 only its top opening in the top portion 11 is visible, while its bottom opening in the bottom portion 13 is not due to the perspective view. However, a cross-section through the entire guidance through-hole 27 with its top and bottom openings can be seen in FIG. 9 as further explained below.

Figure 7:
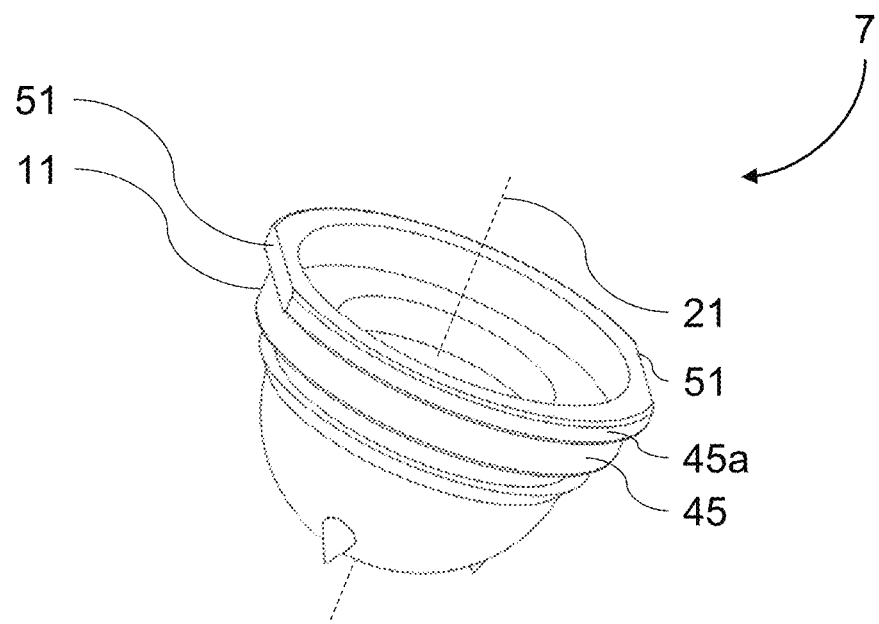
FIG. 7 is a perspective view of a seventh surgical targeting device embodiment similar to the sixth surgical targeting device embodiment of FIG. 6 with a different collar having a bayonet-type interface.

FIG. 7 shows a perspective view of a surgical targeting device 7 similar to the surgical targeting device 6 in FIG. 6. One difference is that the top portion 11 comprises a ring-shaped collar 45 that protrudes laterally from the top portion 11. Another difference is that this ring-shaped collar 45 comprises two opposing lateral cut-outs 51 along parallel planes which extend in parallel to the guidance through-hole central axis 21. These cut-outs 51 form a tool gripping structure provided for the attachment of a removal tool by means of a bayonet-like connection. Hence, the cut-outs 51 form a bayonet-type interface. Alternatively, one cut-out 51 or more than two cut-outs 51 may be provided for the aforementioned purpose.

Figure 8:
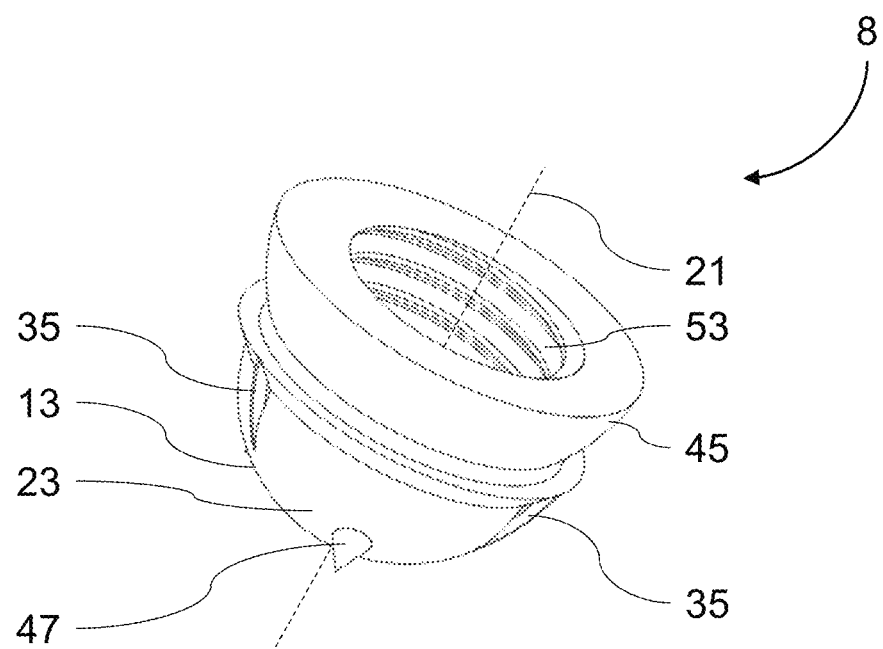
FIG. 8 is a perspective view of an eighth surgical targeting device embodiment similar to the sixth surgical targeting device embodiment of FIG. 6 with additional fins and a collar having additionally an internal thread.

FIG. 8 shows a perspective view of another surgical targeting device 8 similar to the surgical targeting device 6 in FIG. 6. One difference resides in the fact that the outer surface 23 of the bottom portion 13 additionally comprises fins 35 having a function similar to the function of the fin 35 of the surgical targeting device 2 illustrated in FIG. 2. Another difference is that the top portion 11 comprises an internal thread 53. The internal thread 53 forms a tool gripping structure provided for being gripped by a removal tool having a corresponding outer thread as will be described with reference to FIG. 10 below. Alternatively, the top portion 11 may comprise an outer thread for a tool with a corresponding internal thread. Further, the top portion 11 may comprise an internal thread 53 and an outer thread in order to allow an engagement of different removal tools.

It will be appreciated that the tool gripping structures described above with reference to FIGS. 6 to 8 could also be used in each of the embodiments of FIGS. 1 to 5.

Figure 9:
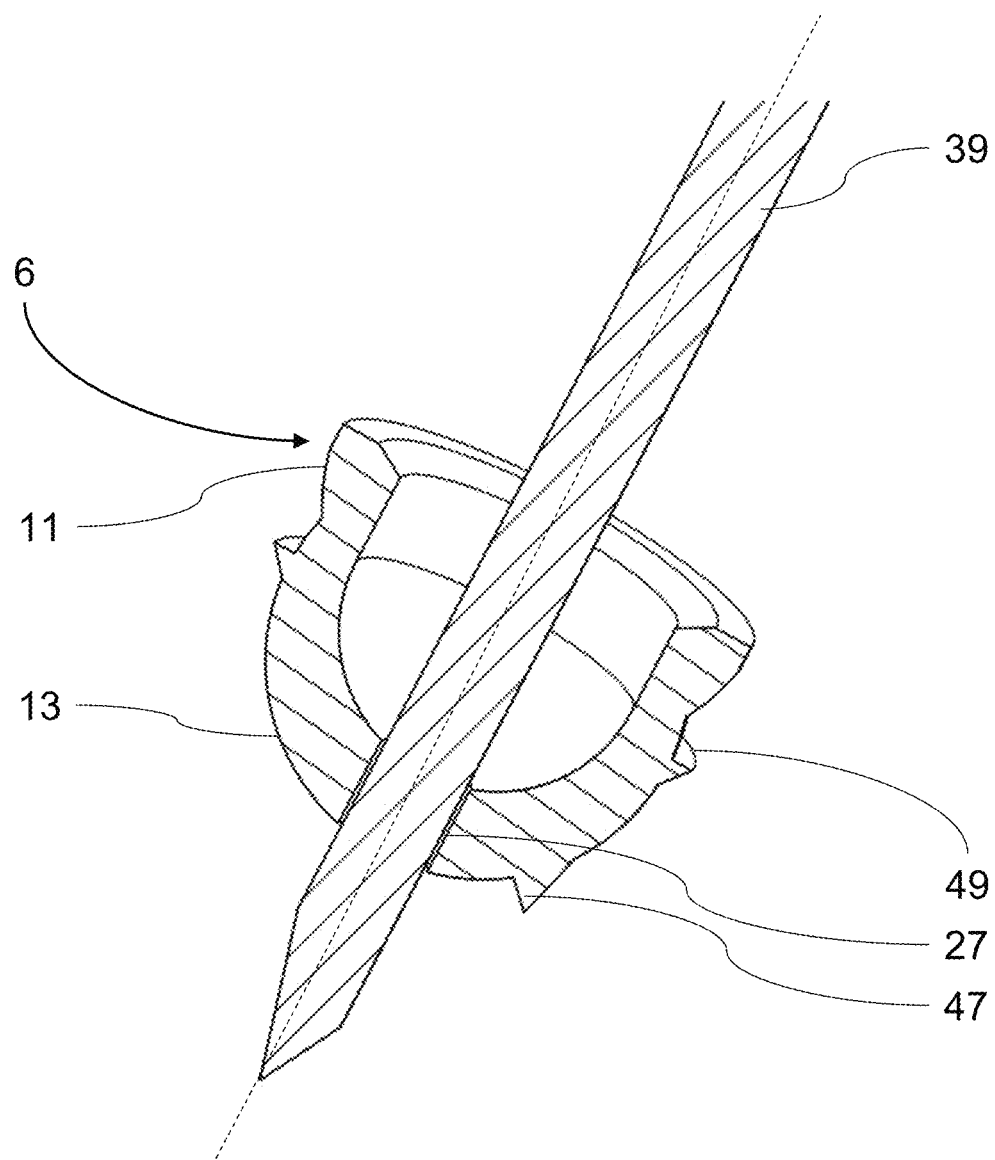
FIG. 9 is a perspective cross-section view of the sixth surgical targeting device embodiment of FIG. 6 with a guidance member inserted through and extending from the longitudinal through-hole.

FIG. 9 shows a perspective cross-section view of the surgical targeting device 6 of FIG. 6 with a guidance K-wire 39 inserted through and extending from its longitudinal through-hole 27 from the top portion 11 towards the bottom portion 13.

Figure 10:
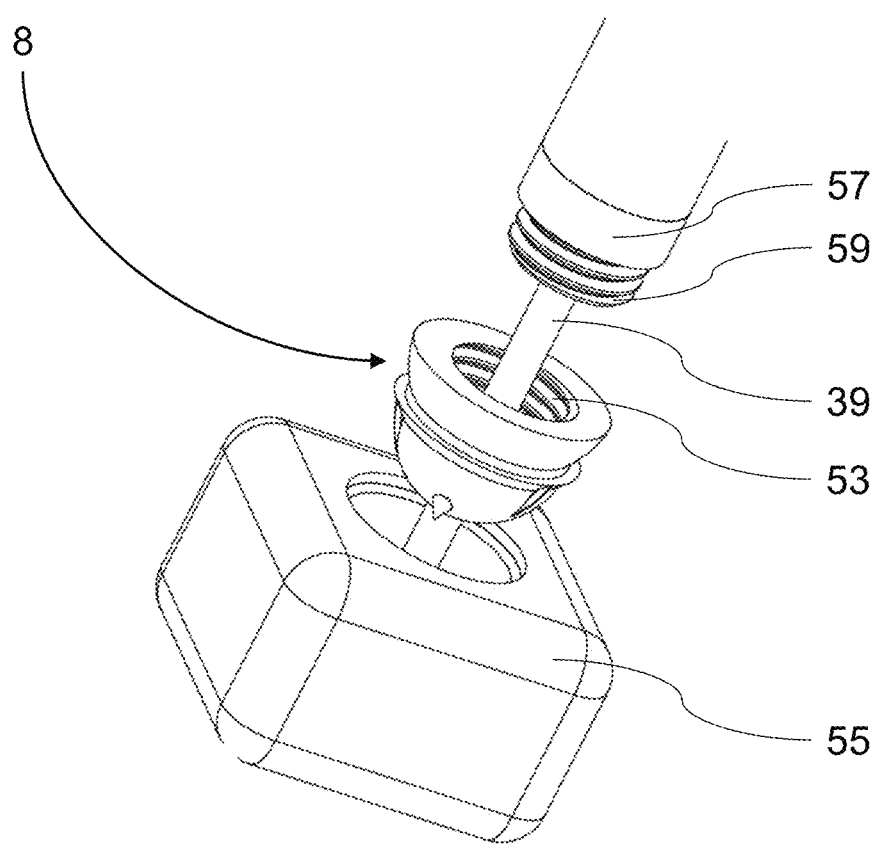
FIG. 10 is a perspective view of the eighth surgical targeting device embodiment of FIG. 8 with a guidance member inserted through and extending from the longitudinal through-hole to be fixed in a bone, and a tool with an outer thread corresponding to the internal thread of the eighth surgical targeting device for removing the surgical targeting device from the bone along and guided by the fixed guidance member.

FIG. 10 shows a perspective view of the surgical targeting device 8 of FIG. 8 with a guidance K-wire 39 inserted through and extending from its longitudinal through-hole 27 to be fixed in trapezium bone 55 (only schematically illustrated), and a tool 57 with an outer thread 59 corresponding to the internal thread 53 of the surgical targeting device 8 for removing the surgical targeting device 8 from the bone 55 along the fixed guidance K-wire 39.

Figure 11:
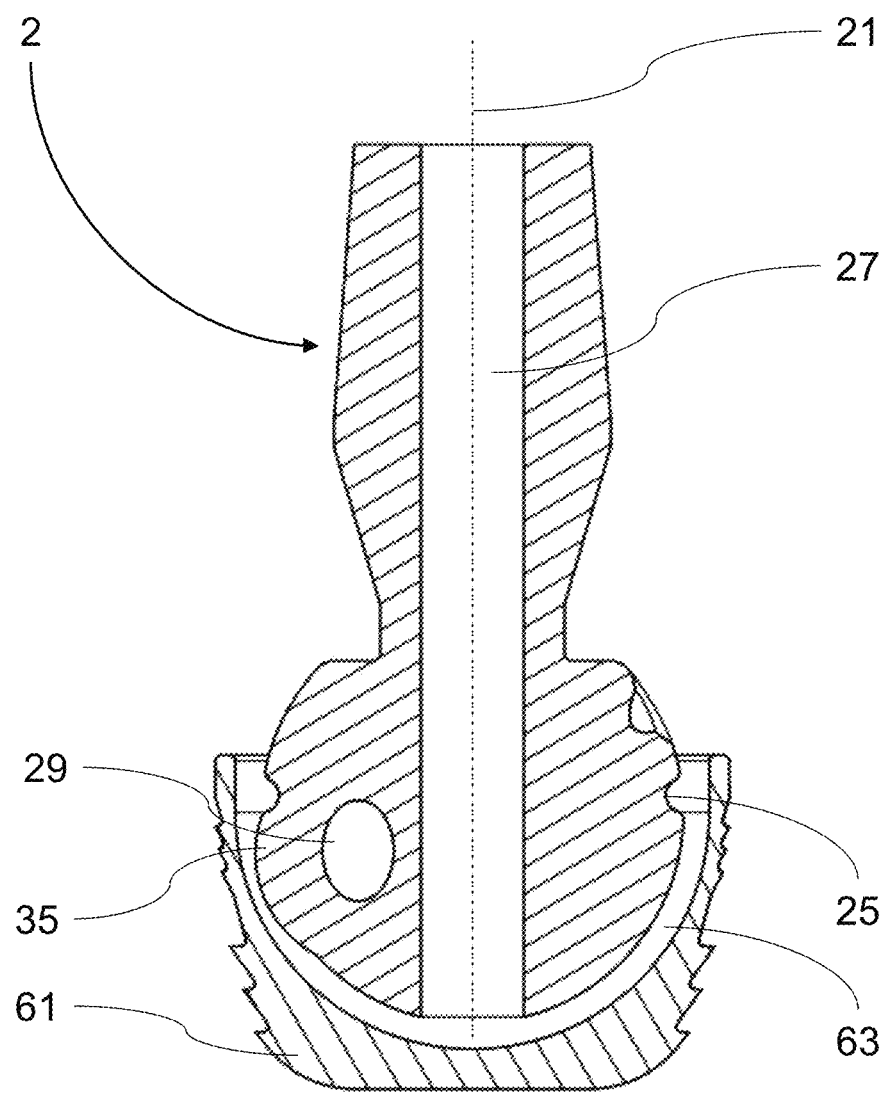
FIG. 11 is a lateral cross-sectional view of the second surgical targeting device in FIG. 2 inserted for illustration purposes only into a joint prosthesis cup, i.e., a socket part of a ball and socket joint implant, to be fixed to the bone in the cavity formed by reaming into the bone along a guidance member fixed to the bone by means of the second surgical targeting device.
Figure 12:
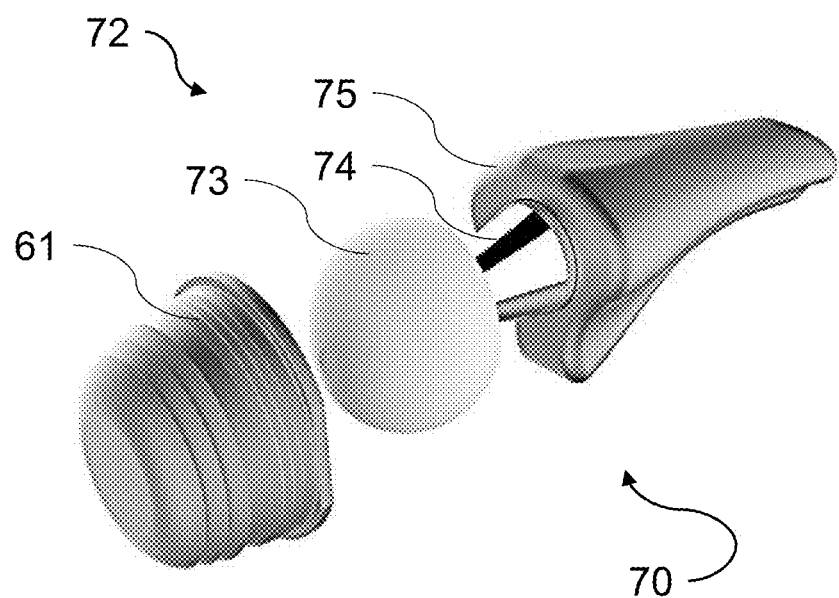
FIG. 12 is a perspective view of a ball and socket joint implant that may be used in system embodiments of the present disclosure.

FIG. 11 shows—for illustration purposes only—a lateral cross-section view of the surgical targeting device 2 of FIG. 2 inserted into a trapezium bone cup implant, i.e., a socket part 61 of a ball and socket joint implant 70 as shown in FIG. 12. The socket part 61 will be permanently inserted into and fixed to a recess formed in the trapezium bone by reaming along a guidance K-wire that has temporarily been fixed to the bone by means of the surgical targeting device 2 or any other of the surgical targeting devices presented herein.

FIG. 11 is intended to illustrate the dimensional relationships between the surgical targeting device of the present embodiments and the actual implant. It should be noted that the outer shape of the implant 61 is conical while the bottom portion 13 of the surgical targeting device 2 is curved, in particular spherically curved.

For the general understanding of the above, the ball and socket joint implant 70 shall be explained in the following with reference to FIG. 12. The ball and socket joint implant 70 is divided into two parts that eventually form the actual artificial joint: a ball part 72 and the socket part 61. Both parts 61, 72 are permanently connected to the respective bones of the natural joint and pivotable relative to each other. The socket part 61 has a concave cup shape with a central opening. The outer surface of the socket part 61 engages with the trapezium bone to permanently remain in the bone while the opening with its concave inner surface remains accessible.

The ball part 72 comprises a convexly curved head 73 that is generally spherical and is configured to snap into the opening of the socket part 61 to be pivotable relative to the socket part 61, as is known in the art. On its side facing away from the socket part 61, the spherically shaped head 73 of the ball part 72 is connected to a shaft 74 followed by a stem 75. The latter is eventually inserted into the other bone of the natural joint opposite the trapezium bone. The shaft 74 may be integral with the head 73 and inserted into the stem 75. In some cases, shaft 74 and stem 75 may be integral.

Figure 13:
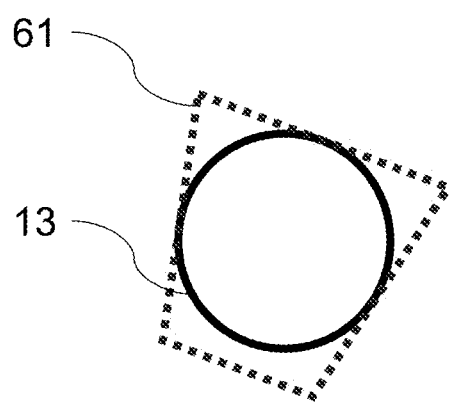
FIG. 13 is a schematic view of a bottom portion of the surgical targeting device fitting into the volume defined by outer dimensions of a socket part of a ball and socket joint implant.

By using one of the above surgical targeting devices, the socket part 61 can be guided to and permanently connected to the trapezium bone in a position and orientation which corresponds best to a desired range of motion of the ball part 72. As illustrated in FIG. 13, the bottom portion 13 of the surgical targeting device fits into a volume defined by the outer dimensions of the socket part 61 of the ball and socket joint implant 70. Depending of the bone reaming, the bottom portion 13 will have a somewhat smaller outer dimension them the socket part 61.

The surgical targeting device allows not only a fast and intuitive placement of a reamer guidance member, e.g., a K-wire, in the trapezium bone but also a more precise placement, since the top portion 11 of the surgical targeting device can be inserted into the joint stem 75 (or in a dummy thereof or in the other bone) so as to simulate the pivotability, i.e., the range of motion, of the artificial joint to be expected once the socket part 61 is permanently fixed to the trapezium bone and connected with the ball part 72 permanently fixed to the other bone. Consequently, the top portion 11 of the surgical targeting device and the portion of the shaft 74 of the ball part 72 capable of being received by the stem 75 may have corresponding outer dimensions.

Any of the above surgical targeting devices may be combined into a surgical system with at least one of the socket part 61 of the ball and socket joint implant 70, a tool 57 for removing the surgical targeting device 1-8 from the temporary engagement with the trapezium bone 55, a guidance member (e.g., K-wire) 39, and at least one auxiliary attachment member (e.g., K-wire) 37 capable of being inserted into the auxiliary through-hole 29 of the surgical targeting device. In some variants, the tool gripping portion may be provided at the bottom portion 13. In such variants, the top portion 11 may not have a dedicated tool gripping portion.

It will be appreciated that use of the above surgical targeting devices is not limited to trapezium bones. As an example, differently sized surgical targeting devices according to the present disclosure could also be used the context of hip replacement surgery.

The invention claimed is:

1. A surgical system, comprising:
  a surgical targeting device for assisting placement of an elongated guidance member in a bone, comprising:
    a bottom portion having a dome-shaped convex outer surface and comprising a guidance through-hole extending along a guidance through-hole central axis for receiving the guidance member; and
    a top portion configured to be gripped by a tool;
  a socket part of a ball and socket joint implant; and
  a ball part of the ball and socket joint implant, the ball part comprising:
    a head,
    a shaft extending from the head, and
    a stem which is capable of receiving at least a portion of the shaft of the ball part;
    wherein the top portion of the surgical targeting device and the portion of the shaft of the ball part capable of being received by the stem have corresponding outer dimensions capable of being received in the stem,
  wherein the bottom portion of the surgical targeting device fits into a volume defined by outer dimensions of the socket part of the ball and socket joint implant.

2. The surgical system according to claim 1, wherein the guidance through-hole extends along the guidance through-hole central axis through the bottom portion and the top portion.

3. The surgical system according to claim 1, wherein the top portion comprises a shaft extending from the bottom portion.

4. The surgical system according to claim 3, wherein the shaft of the surgical targeting device is configured to temporarily be inserted into a stem of an implant or of a dummy thereof.

5. The surgical system according to claim 1, wherein the bottom portion comprises at least one auxiliary through-hole extending through the bottom portion along an auxiliary through-hole central axis and spaced from the guidance through-hole, the at least one auxiliary through-hole being configured to receive an attachment member so that the device becomes temporarily engaged with the bone.

6. The surgical system according to claim 5, wherein the auxiliary through-hole central axis extends obliquely to the guidance through-hole central axis.

7. The surgical system according to claim 5, wherein the guidance through-hole central axis and the auxiliary through-hole central axis do not intersect.

8. The surgical system according to claim 5, wherein the at least one auxiliary through-hole extends from a top opening to a bottom opening in the device, wherein the top opening is further spaced from the guidance through-hole central axis than the bottom opening is spaced from the guidance through-hole central axis.

9. The surgical system according to claim 5, wherein the bottom portion comprises one or more wings laterally protruding from the bottom portion and each comprising at least one of the at least one auxiliary through-hole.

10. The surgical system according to claim 1, wherein the bottom portion comprises at least one protrusion for temporary engagement with the bone.

11. The surgical system according to claim 10, wherein the at least one protrusion includes a fin or a spike.

12. The surgical system according to claim 1, wherein the bottom portion comprises a visual depth marker indicative of a plane extending orthogonally to the guidance through-hole central axis.

13. The surgical system according to claim 12, wherein the visual depth marker is a circumferential marking, groove or rim.

14. The surgical system according to claim 1, wherein the top portion comprises a tool gripping structure configured to be gripped by the tool for removing the surgical targeting device from the bone.

15. The surgical system according to claim 14, wherein the tool gripping structure comprises a neck.

16. The surgical system according to claim 14, wherein the tool gripping structure comprises a thread or a bayonet-type interface.

17. The surgical system according to claim 1, wherein the guidance through-hole central axis extends in a symmetry plane of the surgical targeting device.

18. The surgical system of claim 1, wherein the dome-shaped convex outer surface of the bottom portion of the surgical device is spherically shaped; and the socket part of the ball and socket joint implant has a conically shaped outer surface.

19. A surgical targeting device sized and configured to be temporarily placed in the trapezium bone for assisting placement of an elongated guidance member in the trapezium bone, the surgical targeting device comprising a monolithic body having:
  a bottom portion having a dome-shaped convex outer surface and comprising a guidance through-hole extending along a guidance through-hole central axis for receiving the guidance member; and a top portion configured to be gripped by a tool, the top portion comprises a shaft extending from the bottom portion, wherein the guidance through-hole extends along the guidance through-hole central axis through the bottom portion and the top portion, wherein the shaft is sized and configured to temporarily be inserted into a stem of an implant, wherein the bottom portion comprises at least one auxiliary through-hole extending through the bottom portion along an auxiliary through-hole central axis and spaced from the guidance through-hole, the at least one auxiliary through-hole being configured to receive an attachment member so that the device becomes temporarily engaged with the trapezium bone, wherein the elongated guidance member is a Kirschner wire (K-wire).

* * * * *